United States Patent
Hoshino

(10) Patent No.: US 6,899,869 B2
(45) Date of Patent: May 31, 2005

(54) METHOD OF PREPARING AN ANIMAL MODEL FOR INTERSTITIAL PNEUMONIA

(76) Inventor: Tomoaki Hoshino, 1-8-7, Utsukushigaoka minami, Chikushino-shi, Fukuoka 818-0034 (JP)

(*) Notice: Subject to any disclaimer, the term of this patent is extended or adjusted under 35 U.S.C. 154(b) by 0 days.

(21) Appl. No.: 10/257,965
(22) PCT Filed: Apr. 23, 2001
(86) PCT No.: PCT/JP01/03467
§ 371 (c)(1), (2), (4) Date: Oct. 25, 2002
(87) PCT Pub. No.: WO01/80891
PCT Pub. Date: Nov. 1, 2001

(65) Prior Publication Data
US 2003/0099637 A1 May 29, 2003

(30) Foreign Application Priority Data

Apr. 25, 2000 (JP) .......................... 2000-166845
Jul. 7, 2000 (JP) .......................... 2000-245301
Nov. 13, 2000 (JP) .......................... 2000-345035

(51) Int. Cl.$^7$ .............................................. A61K 45/00
(52) U.S. Cl. ........................... 424/85.2; 514/2; 530/351
(58) Field of Search ........................... 424/85.2; 514/2; 530/351

(56) References Cited

PUBLICATIONS

Arai et al. Interleukin–18 in combination with IL–2 enhances natural killer cell activity without inducing large amounts of IFN–gamma in vivo. J. Interferon & Cytokine Res., Feb. 2000, 20 (2):217–24.*

Bohn et al. IL–18 (IFN–gamma–inducing factor) regulates early cytokine production in, and promotes resolution of, bacterial infection in mice. J. Immunol., 1998, 160:299–307.*

Taniguchi et al. Characterization of anti–human IL–18/IGIF monoclonal antibodies and their application in the measurement of human IL–18 by ELISA. 1997. J. Immuno. Meth., 206:107–113.*

Saito et al.; Elevated Local Production of Neopterin From Alveolar Macrophages in Patients with Internal Lung Diseases; Gen. Pharmac. vol. 27, No. 3, pp. 483–486, 1996. See PCT search report.

Tada et al.; The Significance of Soluble IL–2 Receptors in Rheumatoid Arthritis with Interstitial Pneumonia, Allergy, 41 (3), pp. 428–433, 1992. Partial English translation. See PCT search report.

* cited by examiner

Primary Examiner—Lorraine Spector
Assistant Examiner—Dong Jiang
(74) Attorney, Agent, or Firm—Westerman, Hattori, Daniels & Adrian LLP

(57) ABSTRACT

A method of preparing an animal model of interstitial pneumonia by administering interleukin 18 and interleukin 2. Because the animal model resembles closely human clinical findings, it is precisely capable of screening a drug, which can be expected to be clinically useful.

2 Claims, 2 Drawing Sheets

METHOD OF PREPARING AN ANIMAL MODEL FOR INTERSTITIAL PNEUMONIA

TECHNICAL FIELD

The present invention relates to a remedy for interstitial pneumonia, comprising at least one, or two or more kinds of an interleukin 18 inhibitor and/or an interleukin 2 inhibitor as an active ingredient.

Also the present invention relates to a method of preparing an animal model of a remedy for interstitial pneumonia, and a method of screening a remedy for interstitial pneumonia using said animal model.

BACKGROUND ART

Interstitial pneumonia is a disease that is characterized by cardinal symptoms such as dry cough and shortness of breath and is sometimes accompanied by fever and arthralgia, while other systemic symptoms develop in case interstitial pneumonia is complicated with the systemic disease.

Interstitial pneumonia can be clinically classified into an acute form and a chronic form. Hamman-Rich syndrome is thought to be the acute form. Although steroid is generally used in the treatment of interstitial pneumonia, poor prognosis for interstitial pneumonia often causes pulmonary fibrosis, which leads to severe course. Therefore, there is required a novel remedy for treatment of interstitial pneumonia, as well as prevention and treatment of pulmonary fibrosis.

A proper animal model of interstitial pneumonia has never been known, although it has hitherto been known administering bleomycin or silica to a mouse induces pulmonary fibrosis.

Interleukin 18 (IL-18) is the latest cytokine which was discovered as interferon γ (IFN-γ) inducible factor [IGIF] by macrophages in 1995 [Nature 378, 88–91(1995)]. IL-18 is synthesized as a precursor (pro IL-18) and then converted into an activated type (mature IL-18) by cleavage using an interleukin 1 β-converting enzyme [caspase-1] and so on. A precursor of mouse IL-18 comprises 192 amino acids and an activated one thereof comprises 157 amino acids.

Also a precursor of human IL-18 comprises 193 amino acids and an activated one thereof comprises 157 amino acids.

A receptor of IL-18 belongs to an IL-1 receptor family, and receptor components (IL-18Rα and IL-18Rβ) are known.

It is known that IL-18 acts on helper T cell 1 (Th1) and natural killer cells (NK cells) to induce the production of IFN-γ and also enhances a cytotoxic T cell activity to enhance a cytotoxicity. Therefore, IL-18 is considered to be an inflammatory cytokine which induces Th1 response.

Thus, a relation between type 1 diabetes mellitus [DM], multiple sclerosis and Crohn's disease caused by the Th1 overresponse and IL-18 has attracted special interest.

However, any relation between interstitial pneumonia and IL-18 had never been known.

Interleukin 2 (IL-2) is a cytokine secreted mainly by T cells (CD4+, CD8+) and comprises 133 amino acids. IL-2 is also referred to as a T cell growth factor (TCGF) and causes the growth of T cells. It is known that IL-2 exerts an action on not only T cells, but also B cells, NK cells, macrophages and neutrophilic leukocytes and so on. On the surface of these cells, an IL-2 receptor is expressed. The IL-2 receptor is a complex comprising α chain, β chain and γ chain subunits. The α chain is also referred to as a Tac antigen and comprises 251 amino acids. The γ chain is a second subunit of an IL-4 receptor, IL-7 receptor and an IL-9 receptor, while β chain and γ chain subunits are second and third subunits of an IL-15 receptor.

International Application WO99/51580 discloses that a pyrazole derivative capable of inhibiting the production of IL-2 is used in the treatment of immune-related disease, and also describes pulmonary fibrosis and idiopathic interstitial pneumonia among various diseases listed as the immune-related disease.

However, there is not any concrete description about a therapeutic effect based on the inhibition of the production of IL-2 in any diseases listed in the publication.

DISCLOSURE OF THE INVENTION

An object of the present invention is to provide a novel remedy for interstitial pneumonia, which is used to treat interstitial pneumonia.

Another object of the present invention is to provide a method of preparing an animal model of a remedy for interstitial pneumonia, and a method of screening a remedy for interstitial pneumonia using said animal model.

To clarify a role of IL-18 in the living body, the present inventor had observed a change when IL-18 was administered after lymphocytes were activated by administering IL-2 to a mouse.

As a result, he has found that interstitial pneumonia is caused by administering IL-18 and thus found that IL-18 is closely related to the development of the pathological state of interstitial pneumonia.

The present inventor has supposed that the onset of interstitial pneumonia is suppressed by suppressing overexpression of an action of IL-18 and studied using an IL-18 receptor (IL-18R α) knock-out mouse to prove a hypothesis. As a result, he has confirmed that the onset of interstitial pneumonia is suppressed by suppressing a function of IL-18, and thus completed the present invention.

Furthermore, it has been found that the onset of interstitial pneumonia is also inhibited by suppressing an action of IL-2 because interstitial pneumonia occurs only in the state where lymphocytes are activated, namely, IL-18 coexist with IL-2.

The present invention is directed to a remedy for interstitial pneumonia, comprising at least one, or two or more kinds of an IL-18 inhibitor and/or an IL-2 inhibitor as an active ingredient.

Since it has been found that an animal model of interstitial pneumonia can be prepared by administering IL-18 and IL-2 to a rodent, it became possible to perform screening of a remedy for interstitial pneumonia using the animal model. Therefore, the present invention is directed to a method of preparing an animal model of a remedy for interstitial pneumonia, and a method of screening a remedy for interstitial pneumonia using the animal model.

The present invention will be described in detail hereinafter.

BEST MODE FOR CARRYING OUT THE INVENTION

Figure 1:
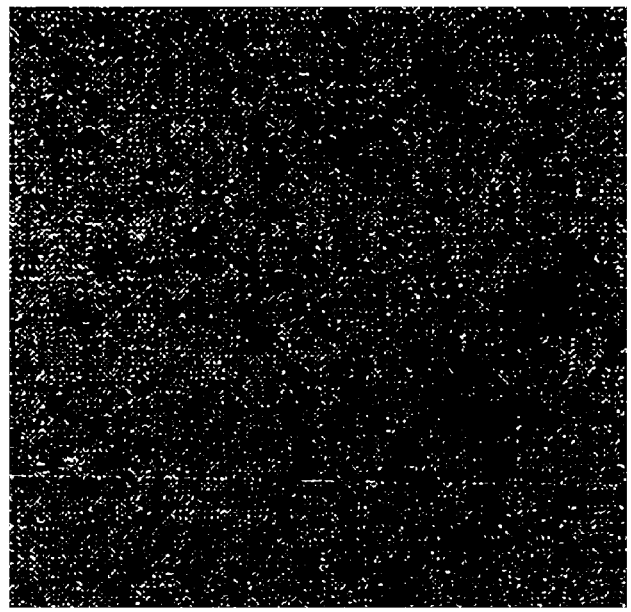
FIG. 1 shows a photomicrograph of a normal C57BL/6 mouse (negative control group).

The IL-18 inhibitor used in the present invention is not specifically limited as far as it is a substance which inhibits the function of over-expressed IL-18.

The IL-18 inhibitor used in the present invention includes, for example, a substance which inhibits conversion of pro IL-18 into mature IL-18. Specific examples of the substance include an inhibitor of cysteine protease. As the inhibitor of cysteine protease, an interleukin 1 β-converting enzyme inhibitor (inhibitor of caspase-1) can be preferably used.

Examples of the IL-18 inhibitor used in the present invention include substances which neutralize an activity of IL-18, such as IL-18-binding protein and anti-IL-18 antibody and so on, and a substance which inhibits binding of IL-18 to an IL-18 receptor. Furthermore, an inhibitor for signal transfer after binding to the IL-18 receptor.

As the IL-18 inhibitor used in the present invention, the substance, which inhibits binding of IL-18 to the IL-18 receptor, is particularly preferred.

Various compounds are known as the interleukin 1 β-converting enzyme inhibitor used in the present invention and specific examples thereof include a peptide derivative described in Japanese Unexamined Patent Publication (Kokai) No. 5-255218, a sulfonamide derivative described in Japanese Unexamined Patent Publication (Kokai) No. 11-147873, a peptide derivative described in National Publication of Translated Version (Kohyo) No. 10-504285, a glycine derivative described in Japanese Unexamined Patent Publication (Kokai) No. 11-147895, and a tetrazole derivative described in International Publication WO97/24339.

The IL-18-binding protein can be prepared in accordance with the method described in the literature [Immunity, 10, 127–136 (1999)].

The monoclonal antibody specific for IL-18 can be prepared in accordance with the method described in the literature [J. Immunol, Methods, 217, 97–102 (1998)].

Specific examples of the substance, which inhibits binding of IL-18 to the IL-18 receptor (IL-18Rα), include the IL-18 receptor protein and a monoclonal antibody specific for a receptor of IL-18.

The monoclonal antibody specific for the receptor of IL-18 may be any of an antibody derived from mammal, a chimera antibody and a humanized antibody.

The IL-18 receptor protein and the monoclonal antibody specific for the receptor of IL-18 used in the present invention can be prepared, for example, in accordance with the method described in Unexamined Patent Publication (Kokai) No. 11-100400.

The IL-2 inhibitor used in the present invention is not specifically limited as far as it is a substance which inhibits the function of over-expressed IL-2.

The IL-2 inhibitor used in the present invention includes, for example, a substance which neutralizes an activity of IL-2, such as an anti-IL-2 antibody, a substance which acts as an antagonist of IL-2, such as IL-2-diphtheria toxin conjugate (IL-2 conjugated protein), and a substance which inhibits binding of IL-2 to an IL-2 receptor. Examples of the substance inhibits binding of IL-2 to the IL-2 receptor include an antibody and a ligand, which are bound to α chain, β chain and/or γ chain subunits of the IL-2 receptor.

The substance which neutralizes an activity of IL-2, such as anti-IL-2 antibody, is described, for example, in Japanese Unexamined Patent Publication (Kokai) No. 60-246322.

The substance which acts as an antagonist of IL-2 is described, for example, in Japanese Examined Patent Publication (Kokoku) No. 6-92318. With respect to an IL-2-diphtheria toxin conjugate preparation, the development of DAB389 IL-2 and ONTAK (trade name) is making steady progress as a remedy for T cell cutaneous lymphoma, psoriasis or the like. ONTAK has already been put on the market in USA as a remedy for T cell cutaneous lymphoma.

Specific examples of the substance, which inhibits binding of IL-2 to the IL-2 receptor, include an antibody specific for a IL-2 receptor.

The antibody specific for the IL-2 receptor is disclosed, for example, in Japanese Unexamined Patent Publication (Kokai) No. 62-56440, Japanese Unexamined Patent Publication (Kokai) No. 5-244982 and Japanese Unexamined Patent Publication (Kokai) No. 7-165795.

The antibody specific for the IL-2 receptor is preferably a monoclonal antibody. As the monoclonal antibody specific for the IL-2 receptor, for example, an anti-IL-2 receptor humanized monoclonal antibody (humanized anti-Tac antibody) is preferably used. The humanized anti-Tac antibody is disclosed in U.S. Pat. No. 5,530,101. Also the humanized anti-Tac antibody has already been put on the market in USA and so on as a rejection inhibitor in kidney transplantation under the trade name of Zenapax.

The remedy for interstitial pneumonia of the present invention can be appropriately administered to a patient in various preparation forms such as preparation for oral administration, injection or inhalant.

The remedy for interstitial pneumonia of the present invention can also be appropriately used in combination with other drugs used for interstitial pneumonia, for example, steroid. Furthermore, it is possible to use two or more kinds of an interleukin 1 β-converting enzyme inhibitor, an IL-18-binding protein, an anti-IL-18 antibody, a monoclonal antibody specific for a receptor of IL-18, an anti-IL-2 antibody, an IL-2-conjugated protein and a monoclonal antibody specific for an IL-2 receptor, which are used in the present invention, in combination.

Various preparations of the remedy for interstitial pneumonia of the present invention can be prepared by a conventional method. Examples of the dosage form suitable for oral administration include tablets, capsules, granules, fine granules, powders and the like, and these preparations are prepared by appropriately mixing at least one, or two or more kinds of an IL-18 inhibitor and/or an IL-2 inhibitor used in the present invention with conventional pharmaceutical additives such as lactose, cornstarch, crystalline cellulose, magnesium stearate, calcium carboxymethyl cellulose, hydroxypropyl cellulose and talc, and using a conventional method.

The injection can be prepared by a conventional method and isotonic agents such as mannitol, sodium chloride, glucose, sorbitol, glycerol, xylitol, fructose, maltose and mannose, stabilizers such as sodium sulfite and albumin, and preservatives such as benzyl alcohol and methyl parahydroxybenzoate can be appropriately added in the preparation.

The injection can also take the form of a freeze-dried preparation soluble upon use. The freeze-dried preparation can be prepared by a conventional method and isotonic agents, stabilizers and preservatives and so on described above can be appropriately added therein.

The inhalant can be prepared by a conventional method and is prepared by dissolving or suspending at least one, or two or more kinds of an IL-18 inhibitor and/or an IL-2 inhibitor used in the present invention in an isotonic sodium chloride solution and appropriately adding isotonic agents such as mannitol, sodium chloride, glucose, sorbitol, glycerol, xylitol, fructose, maltose and mannose, stabilizers such as sodium sulfite and albumin, and preservatives such as benzyl alcohol and methyl parahydroxybenzoate.

In case at least one, or two or more kinds of an IL-18 inhibitor and/or an IL-2 inhibitor used in the present invention are monoclonal antibodies specific for receptor of IL-18 or IL-2, the remedy for interstitial pneumonia of the present invention can be usually used as the injection or inhalant. The injection or inhalant can be prepared by a conventional method.

The dose of the remedy for interstitial pneumonia of the present invention varies depending on the kind of the inhibitor used in the present invention, administration route, pathological state, age and body weight of a patient and the like, but is usually within a range from 0.1 to 1,000 mg per day and the daily dose may be appropriately administered at a time, or in two or three divided portions.

Examples of a rodent used as an animal model of the remedy for interstitial pneumonia included in the present invention include mouse, rat and the like, and a mouse is preferred.

The animal model of interstitial pneumonia included of the present invention can be easily prepared, for example, by continuously administering IL-18 and IL-2 to the mouse as shown Experiment Example 1 described hereinafter.

Also screening of the remedy for interstitial pneumonia can be performed by appropriately administering a test drug to the animal model of interstitial pneumonia thus prepared and examining the effect (for example, survival rate) of the test drug to the model animal.

The effect of the present invention will become apparent from the Experimental results of the following Experiment Example 1 through Experiment Example 3.

EXPERIMENT EXAMPLE 1-(1)

Certification of Onset of Interstitial Pneumonia Due to Administration of IL-2+IL-18 (1)

(1) Experiment Method

With respect to two strains of mice such as C57BL/6 and BALB/c mice, the following experiment was performed. In both strains, all mice were female mice aged 6 weeks.

Mice were divided into groups of 5–10 mice each membered and then continuously subjected to a treatment shown in the following table once a day for 10 days. All mice were sacrificed on the eleventh day.

Sacrificed mice were dissected and all organs were microscopically observed with hematoxylin-eosin (HE) staining.

Commercially available recombinant human IL-2 and recombinant mouse IL-18 were used as IL-2 and IL-18.

TABLE 1

| Groups | Samples (intraperitoneal administration) |
|---|---|
| 1 | PBS 0.2 ml |
| 2 | IL-2 (50000 IU)/0.2 ml PBS |
| 3 | IL-18 (2 µg)/0.2 ml PBS |
| 4 | IL-2 (50000 IU) + IL-18 (0.04 µg)/0.2 ml PBS |
| 5 | IL-2 (50000 IU) + IL-18 (0.1 µg)/0.2 ml PBS |
| 6 | IL-2 (50000 IU) + IL-18 (0.5 µg)/0.2 ml PBS |

TABLE 1-continued

| Groups | Samples (intraperitoneal administration) |
|---|---|
| 7 | IL-2 (50000 IU) + IL-18 (1 µg)/0.2 ml PBS |
| 8 | IL-2 (50000 IU) + IL-18 (2 µg)/0.2 ml PBS |

(2) Experimental Results

C57BL/6 Mice

All mice survived in the control group (group 1), the group of administration of IL-2 alone (group 2) and the group of administration of IL-18 alone (group 3).

In the case of the group wherein IL-2 and IL-18 were simultaneously administered, all mice survived in the group wherein the amount of IL-18 is 0.04 µg (group 4), while a survival rate was within a range from 0 to 10% in the groups wherein the amount is 0.1 µg, 0.5 µg, 1 µg and 2 µg (groups 5 to 8). Consequently, a survival time of a mouse was reduced depending on the amount of IL-18.

BALB/C Mice

All mice survived in the control group (group 1), the group of administration of IL-2 alone (group 2) and the group of administration of IL-18 alone (group 3).

In the case of the group wherein IL-2 and IL-18 were simultaneously administered, a survival rate was within a range from 90 to 100% in the groups wherein the amount of IL-18 is 0.04 µg (group 4) and the group wherein the amount is 0.1 µg (group 5), while a survival rate was within a range from 0 to 20% in the groups wherein the amount is 0.5 µg, 1 µg and 2 µg (groups 6 to 8). Consequently, a survival time of a mouse was reduced depending on the amount of IL-18.

HE staining of the dissected mice revealed that pathological changes are limited to the lung, while no abnormality was found in other organs such as lever, heart, kidney and digestive organs. In the lung, symptoms of interstitial pneumonia were found, for example, lymphocytes infiltrate into interstitium, resulting in partial architectural destruction of alveolus.

A suspension of IL-2 (50,000 IU) and IL-18 (0.2 µg) in 0.2 ml PBS was intraperitoneally administered to C57BL/6 mice, continuously, once a day for 14 days and mice were sacrificed after 15 or more days have passed. As a result, fibrosis of the lung was found in the survived mice.

As is apparent from the above results, mice succumbed to respiratory insufficiency as a result of the onset of interstitial pneumonia depending on the amount of IL-18 in the co-existence of IL-2. Accordingly, it is suggested that interstitial pneumonia can be treated by suppressing expression of an action of IL-18.

EXPERIMENT EXAMPLE 1-(2)

Certification of Onset of Interstitial Pneumonia Due to Administration of IL-2+IL-18 (2)

(1) Experiment Method

With respect to C57BL/6 mice, the following experiment was performed, besides the above Experiment Example 1-(1). All mice were female mice aged 6 weeks.

Mice were divided into groups of 10 mice each membered and then continuously subjected to a treatment shown in the following table once a day for 14 days. All mice were sacrificed on the fourteenth day.

Sacrificed mice were dissected and all organs were microscopically observed with HE staining.

Commercially available recombinant human IL-2 and recombinant mouse IL-18 were used as IL-2 and IL-18.

TABLE 2

| Groups | Samples (intraperitoneal administration) |
| --- | --- |
| 1 | PBS 0.2 ml |
| 2 | IL-2 (100,000 IU)/0.2 ml PBS |
| 3 | IL-2 (100 IU) + IL-18 (0.5 µg)/0.2 ml PBS |
| 4 | IL-2 (1,000 IU) + IL-18 (0.5 µg)/0.2 ml PBS |
| 5 | IL-2 (10,000 IU) + IL-10 (0.5 µg)/0.2 ml PBS |
| 6 | IL-2 (50,000 IU) + IL-18 (0.5 µg)/0.2 ml PBS |
| 7 | IL-2 (100,000 IU) + IL-18 (0.5 µg) /0.2 ml PBS |

(2) Experimental Results

All mice survived in the control group (group 1) and the group of administration of IL-2 alone (group 2).

In the case of the group wherein IL-2 and IL-18 were simultaneously administered, all mice survived in the group wherein the amount of IL-2 is 100 IU (group 3) and the group wherein the amount of IL-2 is 1,000 IU (group 4), while a survival rate was 60% in the group wherein the amount is 10,000 IU (group 5) and all mice died in the group wherein the amount of IL-2 is 50,000 IU (group 6) and the group wherein the amount is 100,000 IU (group 7). Consequently, a survival time of a mouse was reduced depending on the amount of IL-2.

HE staining of the dissected mice revealed that lethal pathological changes are limited to the lung in the group wherein IL-2 and IL-18 were simultaneously administered, while no pathological change to cause death was found in other organs such as lever, heart, kidney and digestive organs. In the lung, almost the same pathological changes as those of lung histopathology of a patient suffering from interstitial pneumonia were found, for example, lymphocytes infiltrate into interstitium rapidly or drastically, resulting in partial architectural destruction of alveolus.

As is apparent from the above results, mice succumbed to respiratory insufficiency as a result of the onset of interstitial pneumonia depending on the amount of IL-2 in the co-existence of IL-18. Accordingly, it is suggested that interstitial pneumonia can be treated by suppressing expression of an action of IL-2.

The results of Experiment Examples 1-(1) and 1-(2) suggested that interstitial pneumonia can be treated by suppressing either of expression of an action of IL-2 and IL-18.

EXPERIMENT EXAMPLE 2

Elucidation of Mechanism of Onset of Interstitial Pneumonia by IL-18 Receptor Knock-out Mouse (1) Experiment Method As laboratory animals, 129/SvJ IL-18 receptor (IL-18Rα) knock-out mice (one group of 5 mice each membered, female mice aged 7 weeks) prepared by the method of K. Hoshino et al. [J. Immunol., 162, 5041–5044 (1999)], and as a control group, 129 Tcr wild type mice (one group of 5 mice each membered, female mice aged 15 weeks) were used.

A suspension of IL-2 (50,000 IU) and IL-18 (1 µg) in 0.2 ml PBS was intraperitoneally administered to both groups of mice, continuously, once a day for 17 days. All mice were sacrificed on the eighteenth day and sacrificed mice were dissected and all organs were microscopically observed with HE staining.

Commercially available recombinant human IL-2 and recombinant mouse 1L-18 were used as IL-2 and IL-18.

(2) Experimental Results

A survival rate of the control group on the eighteenth day was 20%, while all mice in the group of IL-18 receptor (IL-18R α) knock-out mice survived.

HE staining of all dissected wild mice revealed that pathological changes are limited to the lung, while no abnormality was found in other organs such as lever, heart, kidney and digestive organs. In the lung, symptoms of interstitial pneumonia were found, for example, lymphocytes infiltrate into interstitium, resulting in partial architectural destruction of alveolus. In the group of IL-18 receptor (IL-18Rα) knock-out mice, any symptoms of interstitial pneumonia were not found.

As is apparent from the above results, a mechanism of the onset of interstitial pneumonia depends at least on over-expression of IL-18. Thus, it was elucidated that interstitial pneumonia can be treated by suppressing over-expression of an action of IL-18.

EXPERIMENT EXAMPLE 3

Suppression of Bleomycin Pneumonia by IL-18 Knock-out Mouse and IL-18 Receptor α Knock-out Mouse (1) Experiment Method 0.2 ml PBS containing 2 mg of bleomycin was administered through tail vein to normal C57BL/6 female mice aged 6 weeks (one group of 5 mice each membered, body weight of about 20 g), IL-18 knock-out mice (one group of 5 mice each membered, body weight of about 20 g) and IL-18 receptor α knock-out mice (one group of 5 mice each membered, body weight of about 20 g). These normal C57BL/6 mice, IL-18 knock-out mice and IL-18 receptor α knock-out mice were sacrifices on the seventh day and lung tissues were optical-microscopically observed. As the negative control group, the group wherein only a solvent (PBS: 0.2 ml) was administered to normal C57BL/6 mice in the same manner was used.

(2) Experimental Results

Figure 2:
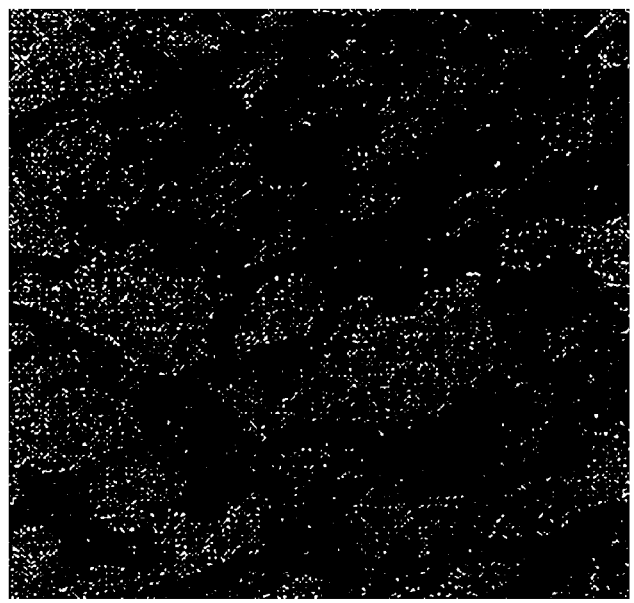
FIG. 2 shows a photomicrograph of a normal C57BL/6 mouse (bleomycin administration group).
Figure 3:
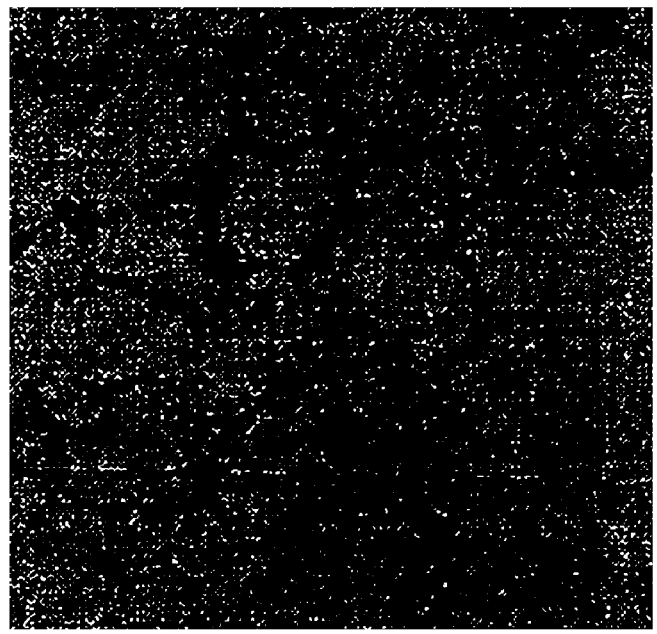
FIG. 3 shows a photomicrograph of an IL-18 knock-out mouse (bleomycin administration group).
Figure 4:
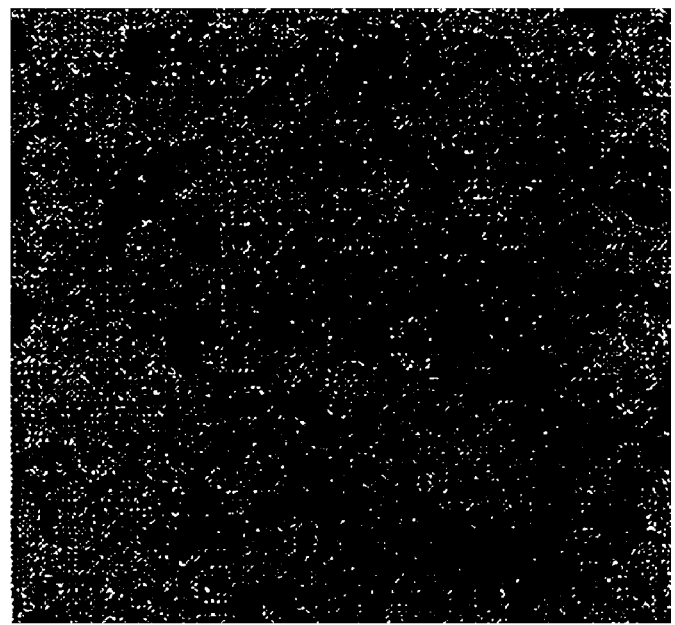
FIG. 4 shows a photomicrograph of an IL-18 receptor α knock-out mouse (bleomycin administration group).

Photomicrographs are shown in FIG. 1 through FIG. 4. In the case of IL-18 knock-out mice and IL-18 receptor α knock-out mice, infiltration of lymphocytes into interstitium and blood vessels of the lung was suppressed as compared with normal C57BL/6 mice.

These results reveal that bleomycin-induced lung injury (pulmonary fibrosis) was suppressed by suppressing IL-18. The following Examples further illustrate the present invention in detail.

EXAMPLE 1

Injection

A PBS containing a monoclonal antibody specific for a receptor of human IL-18 dissolved therein (1 mg/ml) is sterilized by filtration and poured into ampoules in an amount of 5 ml per each ampoule to give injections-containing the monoclonal antibody specific for a receptor of human IL-18(5 mg/ampoule).

EXAMPLE 2

Injection

A PBS containing an-anti-IL-2 receptor humanized monoclonal antibody (humanized anti-Tac antibody) dissolved therein (1 mg/ml) is sterilized by filtration and poured into ampoules in an amount of 100 ml per each ampoule to give injections for drip infusion, containing a humanized anti-Tac antibody (100 mg/ampoule).

INDUSTRIAL APPLICABILITY

The remedy for interstitial pneumonia of the present invention exerts a therapeutic effect by suppressing over-expression of an action of IL-18 which is closely related to the development of the pathological state of interstitial pneumonia. Also the remedy for interstitial pneumonia of the present invention exerts a therapeutic effect by suppressing the action of IL-2 because interstitial pneumonia occurs only in the state where lymphocytes are activated, namely, IL-18 coexist with IL-2.

Since transfer from interstitial pneumonia to pulmonary fibrosis is suppressed by the remedy for interstitial pneumonia of the present invention, the remedy for interstitial pneumonia of the present invention is also useful as a preventive/remedy for pulmonary fibrosis.

The animal model of the remedy for interstitial pneumonia included in the present invention is precisely capable of screening a drug, which can be expected to be clinically useful, by a method of screening the remedy for interstitial pneumonia using the animal model because it resembles closely to the human clinical finding of interstitial pneumonia.

What is claimed is:

1. A method for preparing an animal model of interstitial pneumonia, which comprises the steps of:

providing a rodent; and triggering or increasing interstitial pneumonia in the rodent by administering interleukin 18 and interleukin 2 to the rodent, so as to prepare an animal model of interstitial pneumonia.

2. The method for preparing an animal model of interstitial pneumonia according to claim 1, wherein the rodent is a mouse.

* * * * *